United States Patent
Rangabhatla Gunneswara Subramanya et al.

(10) Patent No.: US 10,980,740 B2
(45) Date of Patent: Apr. 20, 2021

(54) TRANEXAMIC ACID SPRAY FOR KNEE ARTHROPLASTY

(71) Applicant: SHILPA MEDICARE LIMITED, Karnataka (IN)

(72) Inventors: Vara Prasad Rangabhatla Gunneswara Subramanya, Bangalore (IN); Sai Laxmi Aparna Rangabhatla, Bangalore (IN); Ratna Phani Ayalasomayajula, Bangalore (IN)

(73) Assignee: SHILPA MEDICARE LIMITED

( * ) Notice: Subject to any disclaimer, the term of this patent is extended or adjusted under 35 U.S.C. 154(b) by 0 days.

(21) Appl. No.: 16/634,163

(22) PCT Filed: Sep. 11, 2018

(86) PCT No.: PCT/IB2018/056900
§ 371 (c)(1),
(2) Date: Jan. 27, 2020

(87) PCT Pub. No.: WO2019/053579
PCT Pub. Date: Mar. 21, 2019

(65) Prior Publication Data
US 2020/0230047 A1  Jul. 23, 2020

(30) Foreign Application Priority Data
Sep. 12, 2017 (IN) .............................. 201741032141

(51) Int. Cl.
| | | |
|---|---|---|
| A61K 9/00 | (2006.01) | |
| A61K 31/195 | (2006.01) | |
| A61K 47/36 | (2006.01) | |
| A61K 9/12 | (2006.01) | |

(52) U.S. Cl.
CPC .............. *A61K 9/0014* (2013.01); *A61K 9/12* (2013.01); *A61K 31/195* (2013.01); *A61K 47/36* (2013.01)

(58) Field of Classification Search
CPC ........ A61K 9/12; A61K 31/195; A61K 47/36; A61K 9/0014
See application file for complete search history.

(56) References Cited

U.S. PATENT DOCUMENTS

| | | |
|---|---|---|
| 4,515,637 A | 5/1985 | Cioca |
| 5,394,886 A | 3/1995 | Nabai et al. |
| 5,645,849 A | 7/1997 | Pruss et al. |
| 6,045,570 A | 4/2000 | Epstein et al. |
| 6,060,461 A | 5/2000 | Drake |
| 6,096,309 A | 8/2000 | Prior et al. |
| 8,722,081 B2 | 5/2014 | Filatov et al. |
| 2003/0012741 A1 | 1/2003 | Furlan et al. |
| 2011/0052712 A1* | 3/2011 | Eaton ...................... C08L 29/04 424/493 |
| 2015/0038406 A1* | 2/2015 | Buderer ............... A61K 31/351 514/2.3 |
| 2015/0374641 A1* | 12/2015 | Kim ........................ A61K 9/06 514/2.9 |
| 2016/0206773 A1* | 7/2016 | Mousa ................ A61L 26/0076 |
| 2016/0310615 A1 | 10/2016 | Lavik |

FOREIGN PATENT DOCUMENTS

| | | |
|---|---|---|
| FR | 2679772 A1 | 2/1993 |
| JP | 62221357 A | 9/1987 |
| WO | 2001028603 A1 | 4/2001 |

OTHER PUBLICATIONS

Topical application of tranexamic acid for the reduction of bleeding (Review), Ker K, Beecher D, Roberts I, This is a reprint of a Cochrane review, prepared and maintained by the Cochrane Collaboration and published in the Cochrane Library 2013, Issue 7.
Should chitosan and tranexamic acid be combined for improved hemostasis after sinus surgery? Jim Bartley, Department of Surgery, University of Auckland, New Zealand, Medical Hypotheses 81 (2013) 1036-1038.
Topical and intravenous tranexamic acid in reducing blood loss in total knee arthroplasty? A comparative study in Indian population, Chaitanya Krishna, Kumar Pritesh, International Journal of Orthopaedics Sciences 2016; 2(2): 01-04.
Abdel, Matthew P et al. "Intravenous Versus Topical Tranexamic Acid in Total Knee Arthroplasty: Both Effective in a Randomized Clinical Trial of 640 Patients." The Journal of bone and joint surgery. American vol. 100,12 (2018): 1023-1029.

* cited by examiner

*Primary Examiner* — Doan T Phan

(57) ABSTRACT

The present invention relates to novel formulations comprising a sprayable composition comprising tranexamic acid and chitosan for use in the treatment of wounds or injuries, in particular for use as a topical hemostatic composition or for surgical intervention and the process for preparation thereof.

5 Claims, 2 Drawing Sheets

Plotting Time [min]/Volume [ml]

Time (mins.)

Plotting Time [min]/ T/V [min/ml]

time (min)    y=0.000807x+0.00856
              $R^2$=0.986

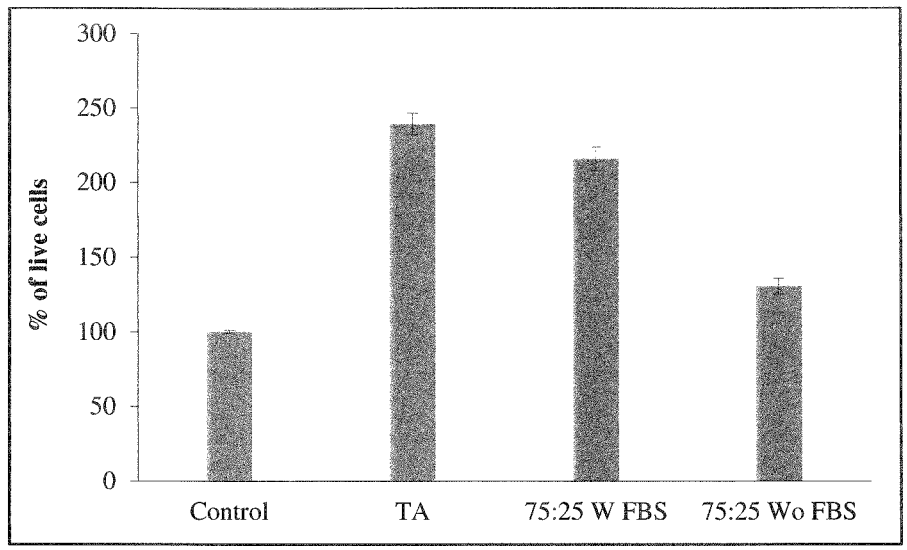

Figure 2. Cell proliferation effect of Tranexamic acid on L929 cell line. Cytotoxic effect of Tranexamic acid were assessed by MTT method with different composition of Tranexamic acid follows 100 %, 75:25 (with FBS), 75:25 (without FBS) and control for 4 hr.

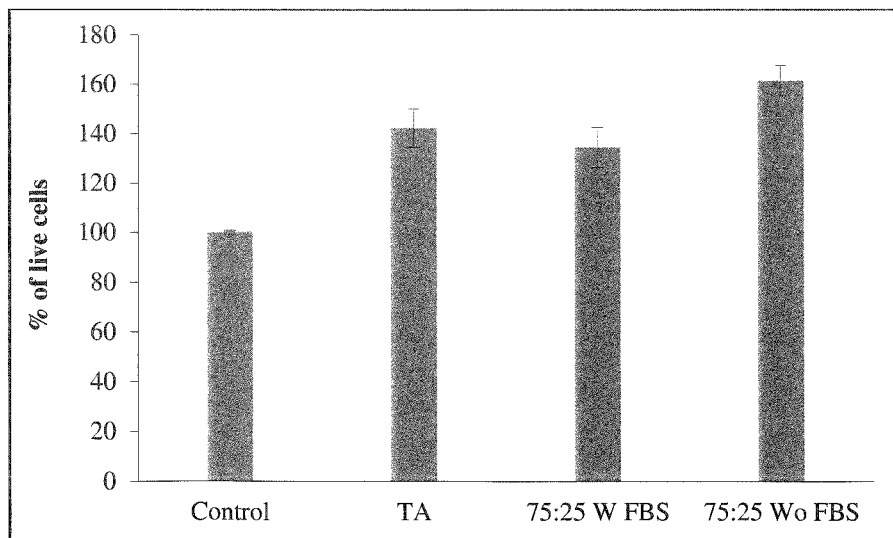

Figure 3. Cell proliferation effect of Tranexamic acid on L929 cell line. Cell proliferation effect of Tranexamic acid were assessed by MTT method with different composition of Tranexamic acid follows 100 %, 75:25 (with FBS), 75:25 (without FBS) and control for 24 hr.

TRANEXAMIC ACID SPRAY FOR KNEE ARTHROPLASTY

FIELD OF THE INVENTION

The present invention relates to novel formulations comprising a sprayable composition comprising tranexamic acid and chitosan for use in the treatment of wounds or injuries, in particular for use as a topical hemostatic composition or for surgical intervention.

BACKGROUND OF THE INVENTION

The use of hemostatic agents provides for control of bleeding in surgical procedures.

WO01/28603 relates to an injectable formulation for delivery of a composition comprising an osteogenic protein and a hemostatic gelatin foam paste as well as to a method of making a hemostatic gelatin foam paste suitable for injecting osteogenic protein, the method comprising hydration of Gelfoam® powder with glutamic acid buffer.

U.S. Pat. No. 5,394,886 relates to a skin biopsy plug wherein the plug is a porous sponge made from gelatin material, which is implanted into a wound, swells, absorbs blood, and is completely absorbed in the patient. It relates to a combination of the punch (the blade for excising skin) and the plug. The plug used is the commercially available Gelfoam®.

Gelfoam® is a commercially available product providing powdered gelatin for application on to bleeding surfaces as a hemostatic agent. The powdered gelatin is provided in a full glass jar with a metal lid or in a sachet, each of which are to be opened and the contents of which, i.e. the gelatin, are to be poured into a sterile beaker or bowl.

U.S. Pat. No. 5,645,849 claims a hemostatic patch comprising a biodegradable gelatin matrix, a hemostatic-promoting amount of thrombin and epsilon aminocaproic acid.

JP62221357 discloses a skin ointment for promoting a hemostatic effect comprising thermoplastic resin or rubber dissolved in solvent and contains dispersed gelatin powder. The product is an ointment comprising thermoplastic resin or rubber and a fine powder of collagen, gelatin or chitosan.

FR2679772 relates to particulate material to create an embolism comprising a polymer coated with a hemostatic or thrombotic agent. The hemostatic agent may be a finely divided gelatin powder.

U.S. Pat. No. 6,096,309 relates to a hemostatic composition comprising thrombin and a mixture of non-microfibrillar collagen and microfibrillar collagen in an aqueous medium wherein the microfibrillar collagen has an average fibril diameter of about 3-30 nm.

U.S. Pat. No. 4,515,637 relates to both a method of forming a collagen-thrombin hemostatic composition and to a lyophilized collagen product, comprising collagen and thrombin.

U.S. Pat. No. 6,045,570 relates to a gelatin powder for use as a hemostatic agent and to a biological sealant comprising a gelatin slurry which includes milled gelatin powder. The slurry preferably comprises Gelfoam® powder mixed with a diluent selected from saline and water. The slurry demonstrates superior flow characteristics in that it exhibits minimal latency and can be easily injected or introduced through catheter lumens, especially small lumens. The product therefore has very fluid characteristics.

U.S. Pat. No. 8,722,081 discloses the hemostatic textile material to stop bleeding, it consists of tranexamic acid, dialdehyde cellulose carrier, blood coagulation factor and bacteriolytic agent. Tranexamic acid is an antifibrinolytic agent that competitively inhibits the activation of plasminogen to plasmin. Tranexamic acid is a competitive inhibitor of plasminogen activation, and at much higher concentrations, a noncompetitive inhibitor of plasmin, i.e., actions similar to aminocaproic acid. Tranexamic acid is about 10 times more potent in vitro than aminocaproic acid. Tranexamic acid binds more strongly than aminocaproic acid to both the strong and weak receptor sites of the plasminogen molecule in a ratio corresponding to the difference in potency between the compounds. Tranexamic acid competitively inhibits activation of plasminogen (via binding to the kringle domain), thereby reducing conversion of plasminogen to plasmin (fibrinolysin), an enzyme that degrades fibrin clots, fibrinogen, and other plasma proteins, including the procoagulant factors V and VIII. Tranexamic acid also directly inhibits plasmin activity, but higher doses are required than are needed to reduce plasmin formation.

US2003/0012741 relates to a process for preparing micronized collagen. It is stated that the particle size should not exceed 20 µm in order to optimize adhesion to the wound surface.

US2015/0038406 relates to a pharmaceutical composition of tranexamic acid and also consists of antibiotic, aesthetic agent, NSAID and excipient or carrier that facilitates local administration.

US2016/0310615 relates to a spray composition comprising a co-block polymer coupled with a water soluble polymer, and a polymer delivery solvent.

Various hemostatic spray for control of bleeding from wounds are commercially available as Traumacel S® a hemostatic dusting powder in a pressurized spray, the active component being a hydrogen calcium salt of oxidized cellulose; Traumacel P® a powdered hemostatic agent comprising a calcium salt of oxidized cellulose (carboxymethylcellulose calcium) which is applied as dry powder onto a bleeding area; Avitene® is a microfibullar collagen hemostat "flour" typically applied dry and Arista® is a hemostatic spray based on microporous polysaccharide hemospheres as described in U.S. Pat. No. 6,060,461 relating to particles, in particular dextran particles, having a particle size from 0.5-1000 µm and an average pore diameter from 0.5-1000 nm. It is disclosed that such particles may be used for enhancing clot formation on a wound by administering the particles in the form of a dry powder.

Katharine Ker et al, Cochrane Database Syst Rev. 2013 Jul. 23; (7): (Topical application of tranexamic acid for the reduction of bleeding) discloses the effects of the topical administration of tranexamic acid in the control of bleeding.

Jim Bartley et al, Med Hypotheses. 2013 December; 81(6):1036-8: (Should chitosan and tranexamic acid be combined for improved hemostasis after sinus surgery) discloses the chitosan combined with a hemostatic agent such tranexamic acid as well as improving hemostatic control should lead to improved clinical outcomes after endoscopic sinus surgery, however this document does not disclose the amount of chitosan and tranexamic acid concentration used for improving hemostatic control after endoscopic sinus surgery.

Hemostatic control is also a part of total knee arthroplasty. Total knee arthroplasty is a major surgical procedure, which is carried out with tourniquet, causing major blood loss in post-operative period due to dramatically increased perfusion in the limb and enhanced fibrinolysis.

Chaitanya Krishna et al, International Journal of Orthopaedics Sciences 2016; 2(2): 01-04: (Topical and intravenous tranexamic acid in reducing blood loss in total knee arthroplasty? A comparative study in Indian population) discloses that topical tranexamic acid and intravenous tranexamic acid are equally efficacious and its recommended for use of tranexamic acid for reduction of peri- and post-operative blood loss in Total knee arthroplasty patients. The topical tranexamic acid reduces the systemic side effects, and topical tranexamic acid in one group is given as tranexamic acid 2 gm in the intra-articular drain and drain was clamped for one hour and then opened to retained the tranexamic acid in the joint space.

Abdel et al, J Bone Joint Surg Am. 2018; 100:1023-9; (Intravenous Versus Topical Tranexamic Acid in Total Knee Arthroplasty) discloses that both intravenous and topical tranexamic acid were effective in reducing calculated blood loss and transfusion rates in patients undergoing elective total knee arthroplasty. The topical tranexamic acid used in this study is 3 gm of tranexamic acid diluted in 45 mL of normal saline solution (total volume of 75 mL) and topically applied after cementation.

However, there exists a need to develop the pharmaceutical composition of spray for treating wounds or injuries, in particular for use as a topical hemostatic composition or for surgical intervention. The present invention relates more specifically to a topical spray composition comprising tranexamic acid and chitosan.

SUMMARY OF THE INVENTION

In one object, the present invention provides herein, compositions consisting essentially of a therapeutically effective amount of tranexamic acid and an excipient that facilitates local administration, and methods of use thereof for treating bleeding in a subject in need thereof comprising locally administering to the subject the compositions.

In another object, the present invention further provides the tranexamic acid spray consisting of tranexamic acid, water soluble polymer, penetration enhancers, stabilizing polymer and water.

In another object, the present invention provides the topical spray composition consisting of tranexamic acid, chitosan, polyethylene glycol, polysorbate 80, polyvinyl pyrrolidone and water.

BRIEF DESCRIPTION OF DRAWINGS

FIG. 2 discloses the cell proliferation of spray composition of example-5, as compared with control for 4 hours.

FIG. 3 discloses the cell proliferation of spray composition of example-5, as compared with control for 24 hours.

DETAILED DESCRIPTION OF THE INVENTION

Figure 1:
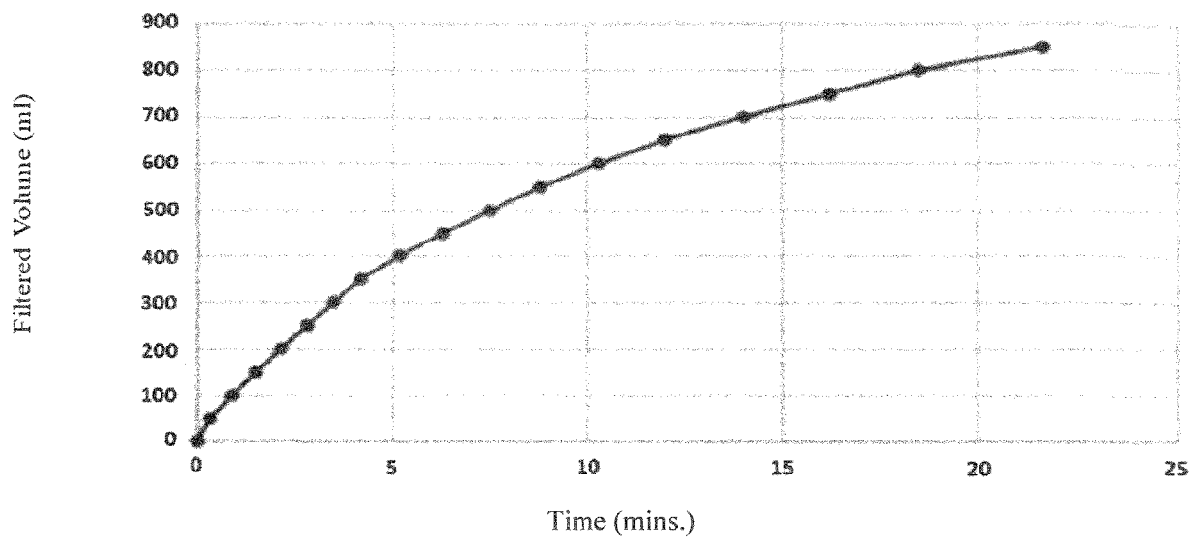
FIG. 1 discloses the sterilization process by filtration of one-liter spray composition as disclosed in example-5 using a pre-filter of 8 μm followed by 0.45 μm and 0.22 μm at a constant pressure of 1.5 bar with a filter surface area of 13 cm².
Figure 1:
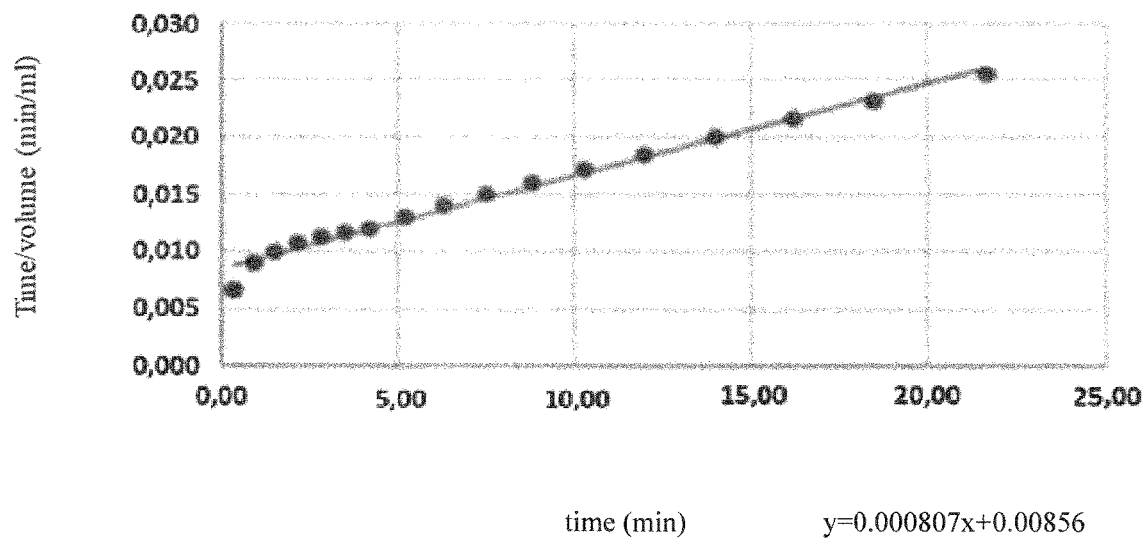

In describing and claiming the present invention, the following terminologies will be used in accordance with the definitions set out below.

The term "Wound" as used herein refers to any damage to any tissue of a patient which results in the loss of blood from the circulatory system and/or any other fluid from the patient's body. The damage may have been caused by any agent or source, including traumatic injury, infection or surgical intervention. A wound may be in a soft tissue, such as an organ, or in hard tissue, such as bone. The tissue may be an internal tissue, such as an organ or blood vessel, or an external tissue, such as the skin. The loss of blood may be internal, such as from a ruptured organ, or external, such as from a laceration.

The term "bleeding" as used herein refers to conditions where blood flows through a break in the skin or mucosa of a subject. Non-limiting examples of bleeding includes a wound selected from the group consisting of a) minor abrasions, cuts, scrapes, scratches, burns, sunburns, ulcers, internal venous bleeding, external venous bleeding, and b) surgical interventions selected from gastrointestinal surgery, surgery on parenchymal organs; surgical interventions in the ear, nose and throat area (ENT), cardiovascular surgery, aesthetic surgery, spinal surgery, neurological surgery; lymphatic, biliary, and cerebrospinal (CSF) fistulae, air leakages during thoracic and pulmonary surgery, thoracic surgery, orthopaedic surgery including knee arthroplasty and hip arthroplasty; gynaecological surgical procedures; vascular surgery and emergency surgery, liver resection, and soft tissue injury or surgery.

The term "total knee arthroplasty" as used herein refers to surgical treatment of knee Pain which comprises 1) Partial knee replacement: The surgeon replaces the damaged portions of the knee with plastic and metal parts and 2) Total knee replacement: In this procedure, the knee is replaced with an artificial joint. It requires a major surgery and hospitalization.

The terms "local administration" and "locally administering" as used herein refer to treatment of bleeding by administering at sites proximate to the bleeding. In certain embodiments, "local administration" or "locally administering" refers to external administration at the site of a wound. In other embodiments, "local administration" or "locally administering" refers to installations, such as knee installation, nasal instillation, bladder instillation, and rectal instillation The term "spray", as used herein, means to dispense the composition as a mass or jet of droplets from a dispensing system.

As used herein in connection with numerical values, the terms "about" mean +/−10% of the indicated value, including the indicated value.

The present invention provides herein, compositions consisting essentially of a therapeutically effective amount of tranexamic acid and pharmaceutically acceptable excipients that facilitates local administration, and methods of use thereof for treating bleeding in a subject in need thereof comprising locally administering to the subject the compositions.

The present invention provides a composition that can treat wounded tissue, including wounded tissue resulting from a traumatic injury or other severe and/or uncontrolled bleeding conditions, such as surgery. The present invention also provides a method of treating wounded mammalian tissue, particularly human tissue.

In one embodiment of the invention, the pharmaceutical composition of the invention is a topical spray.

In another embodiment of the invention, the topical spray composition comprises tranexamic acid and pharmaceutically acceptable excipients.

In embodiments of the invention, topical spray composition comprises tranexamic acid from about 1% to about 10% of tranexamic acid based on the total weight of the composition, and more preferably 1% w/w, 1.5% w/w, 2% w/w, 2.5% w/w, 3% w/w, 3.5% w/w, 4% w/w, 4.5% w/w, 5% w/w, 5.5% w/w, 6% w/w, 6.5% w/w, 7% w/w, 7.5% w/w, 8% w/w, 8.5% w/w, 9.5% w/w and 10% w/w.

In a still another embodiment, the topical spray composition comprises tranexamic acid, water soluble polymer, penetration enhancers and stabilizing polymer.

Examples of the water soluble polymer is selected from the group consisting of polyethylene glycol (PEG), branched PEG, polysialic acid (PSA), carbohydrate, polysaccharides, pullulan, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethyl formal) (PHF), 2-m ethacryloyloxy-2'-ethyltrimethylammoniumphosphate (MPC), polyethylene glycol propionaldehyde, copolymers of ethylene glycol/propylene glycol, monomethoxy-polyethylene glycol, carboxymethylcellulose, polyacetals, poly-1,3-dioxolane, poly-1,3,6-trioxane, ethylene/maleic anhydride copolymer, poly (β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and combinations or mixtures thereof. Preferably, the water soluble polymer is selected from chitosan, and chitosan is preferably used in the pharmaceutical spray composition of about 0.1% to about 1% based on the total weight of the composition. Chitosan is dissolved in glacial acetic acid to form the solution and glacial acetic acid is preferably used in the concentration of about 0.1% to about 2% based on the total weight of the composition.

In a specific embodiment, the topical spray composition comprises tranexamic acid and chitosan.

In a further embodiment, the topical spray composition consists essentially of tranexamic acid chitosan.

In still a further embodiment, the topical spray composition consists of tranexamic acid chitosan.

Examples of the permeation enhancers are selected from glycol ethers, fatty acids, fatty acid esters, glycol esters, glycerides, azones, polysorbates, alcohols, dimethyl sulfoxide, and mixtures thereof. Preferred permeation enhancers for use herein include, but are not limited to, diethylene glycol monoethyl ether (Transcutol), Oleyl alcohol, Oleic acid, Azone (Laurocapram or 1-n-Dodecyl azacycloheptan-2-one), Propylene glycol mono- and diesters of fats and fatty acids (e.g. propylene glycol monocaprylate, propylene glycol monolaurate), Triglycerides and lipids (e.g. linoleic acid), macrogolglycerides or Polyethylene glycol glycerides and fatty esters (e.g. stearoyl macrogolglycerides, oleoyl macrogolglycerides, lauroyl macrogolglycerides, Oleyl macrogol-6-glycerides, lauroyl macrogol-6 glycerides), Glycerides and fatty acid esters of polyethylene glycol 400, Polyoxyl 40 Hydrogenated Castor Oil (Cremophor™ RH 40), Polysorbate 80, Dodecylazacycloheptanone, SEPA such as described in U.S. Pat. No. 4,861,764 (e.g. 2-n-nonyl-1, 3-dioxolane), and mixtures thereof. Preferred mixture of permeation enhancers are selected from polyethylene glycol 400 and polysorbate 80. Penetration enhancers preferably used in the pharmaceutical spray composition of about 1% to about 7% based on the total weight of the composition, preferably polysorbate 80 is used in the range of about 0.1% to about 10% based on the total weight of the composition and polyethylene glycol is used in the range of about 1% to about 5% based on the total weight of the composition.

Example of the stabilizing polymer include recurring structural units containing an amide group. In general, it has been found that polyvinyl pyrrolidone having a wide range of average molecular weights give excellent aerosol pharmaceutical compositions, in particular suspensions. Particularly preferred embodiments of the invention are when the stabilizing polymer is polyvinylpyrrolidone (PVP), also known as povidone. Different types of PVP may be characterized by their viscosity in solution, expressed as a K-value (see European Pharmacopoeia, $5^{th}$ ed., 2004, vol. 2, page 2289). Preferably the K-value of the PVP used is between 10 and 150, more preferably between 15 and 80, more preferably between 20 and 40, most preferably about PVP K30. Stabilizing polymer preferably used in the pharmaceutical spray composition of about 0.1% to about 0.5% based on the total weight of the composition.

In another embodiment the topical spray composition comprises tranexamic acid, chitosan, polyethylene glycol, polysorbate 80, polyvinyl pyrrolidone, glacial acetic acid and water.

In a further embodiment the topical spray composition consists essentially of tranexamic acid, chitosan, polyethylene glycol, polysorbate 80, polyvinyl pyrrolidone, glacial acetic acid and water.

In still a further embodiment the topical spray composition consists of tranexamic acid, chitosan, polyethylene glycol, polysorbate 80, polyvinyl pyrrolidone, glacial acetic acid and water.

In a specific embodiment, the topical spray composition consists of
(a) about 1% to about 10% tranexamic acid,
(b) about 0.1% to about 1% water soluble polymer,
(c) about 1% to about 7% penetration enhancers,
(d) about 0.1% to about 0.5% stabilizing polymers
(e) glacial acetic acid and
(f) water In another embodiment the topical spray composition comprises of about 1% w/w to about 10% w/w of tranexamic acid, about 0.1% w/w to about 1% w/w of chitosan, about 1% w/w to about 5% w/w of polyethylene glycol, about 0.1% to about 1% of polysorbate 80, about 0.1% to about 0.5% of polyvinyl pyrrolidone, glacial acetic acid and water.

In a further embodiment the topical spray composition consists essentially of about 1% w/w to about 10% w/w of tranexamic acid, about 0.1% w/w to about 1% w/w of chitosan, about 1% w/w to about 5% w/w of polyethylene glycol, about 0.1% to about 1% of polysorbate 80, about 0.1% to about 0.5% of polyvinyl pyrrolidone, glacial acetic acid and water.

In a still further embodiment the topical spray composition consists of about 1% w/w to about 10% w/w of tranexamic acid, about 0.1% w/w to about 1% w/w of chitosan, about 1% w/w to about 5% w/w of polyethylene glycol, about 0.1% to about 1% of polysorbate 80, about 0.1% to about 0.5% of polyvinyl pyrrolidone, glacial acetic acid and water.

In another embodiment the topical spray composition comprises of about 10% tranexamic acid, about 1% of chitosan, about 5% of polyethylene glycol, about 0.2% of polysorbate 80, about 0.25% polyvinyl pyrrolidone, glacial acetic acid and water.

In a further embodiment the topical spray composition consists essentially of about 10% tranexamic acid, about 1% of chitosan, about 5% of polyethylene glycol, about 0.2% of polysorbate 80, about 0.25% polyvinyl pyrrolidone, glacial acetic acid and water.

In a still further embodiment the topical spray composition consists of about 10% tranexamic acid, about 1% of chitosan, about 5% of polyethylene glycol, about 0.2% of polysorbate 80, about 0.25% polyvinyl pyrrolidone, glacial acetic acid and water.

In a specific embodiment, the present invention discloses a topical spray composition comprising tranexamic acid, chitosan, polyethylene glycol, polysorbate 80, polyvinyl pyrrolidone and water prepared by a process comprising the steps of
  a) dissolving Chitosan in 1% glacial acetic acid
  b) dissolving tranexamic acid in above solution
  c) adding polyethylethylene glycol, polysorbate 80, polyvinyl pyrrolidone and water to above solution and
  d) sterilization by filtration In embodiments of the invention after the preparation of topical spray composition comprising tranexamic acid, chitosan, polyethylene glycol, polysorbate 80, polyvinyl pyrrolidone, acetic acid and water, the inventors have sterilized the spray composition by moist heat sterilization at 121° C. for 10 minutes and 20 minutes respectively and found that there was change in colour of solution due to depolymerisation of chitosan. The inventors of the present invention have surprisingly found that the topical spray composition is sterilized by filtration method using a pre-filter of 8 μm followed by 0.45 μm and 0.22 μm at a constant pressure of 1.5 bar with a filter surface area of 13 $cm^2$ for one-liter topical spray composition and no decolouration of composition was observed. The time vs filtration rate was depicted in FIG. 1 and filtration time for one-liter spray composition was found to be 12.2 minutes.

In another embodiment the topical spray composition of the present invention is used for treating a wound or reducing bleeding at haemorrhaging site.

In a specific embodiment the topical spray composition of the present invention is used for the topical treatment of a wound, and the wound is selected from the group consisting of a) minor abrasions, cuts, scrapes, scratches, burns, sunburns, ulcers, internal venous bleeding, external venous bleeding, and b) surgical interventions selected from gastrointestinal surgery, surgery on parenchymal organs; surgical interventions in the ear, nose and throat area (ENT), cardiovascular surgery, aesthetic surgery, spinal surgery, neurological surgery; lymphatic, biliary, and cerebrospinal (CSF) fistulae, air leakages during thoracic and pulmonary surgery, thoracic surgery, orthopaedic surgery; gynaecological surgical procedures; vascular surgery and emergency surgery, liver resection, and soft tissue injury or surgery.

In another embodiment the topical spray composition of the present invention is topically applied to a traumatic injury in the battle field, a wound or during or after surgery.

In yet another embodiment of the invention, the spray composition of present inventing is used for minor abrasions, cuts, scrapes, scratches, burns, sunburns, ulcers and other skin injuries and irritations, such as bleeding during and post-surgery, and uncontrolled internal and external haemorrhage from heavy trauma and/or battlefield wounds.

In a further embodiment of the invention is provided a method of treating a wound or reducing bleeding at a haemorrhaging site, or the use of a composition according to the invention for hemostasis, tissue sealing and tissue gluing, wherein application or use of the pharmaceutical composition further comprises the application of moderate manual pressure for not less than about 30 seconds, or not less than about 60 seconds, or not less than about 2 minutes, or not less than about 3 minutes, or not less than about 5 minutes, or not less than about 7 minutes, or not less than about 10 minutes, or longer.

In a most preferred embodiment of the invention is provided a pharmaceutical spray composition comprising tranexamic acid and chitosan for use in surgical interventions such as such as in the gastrointestinal system, e.g. the esophagus, stomach, small intestine, large intestine, bowel, rectum, on parenchymal organs such as the liver, pancreas, spleen, lungs, kidney, adrenal glands, lymph and thyroid glands; surgical interventions in the ear, nose and throat area (ENT) including dental surgery, epistaxis, cardiovascular surgery, such as carotid endarterectomy, femoropopliteal bypass or coronary artery bypass grafting (CABG); aesthetic surgery, spinal surgery, neurological surgery, such as posterior lumbar interbody fusion, microdiscectomy or craniotomy; lymphatic, biliary, and cerebrospinal (CSF) fistulae, air leakages during thoracic and pulmonary surgery, thoracic surgery including surgery of the trachea, bronchi and lungs; orthopaedic surgery, such as knee or hip arthroplasty, total knee arthoplasty; gynaecological surgical procedures such as caesarian section, hysterectomy, fibroid surgery; vascular surgery, such as shunts; urological, bone (e.g. spongiosa resection), and emergency surgery. Particularly preferred surgical interventions include orthopaedic surgery, liver resection, soft tissue injury/surgery and vascular surgery.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example-1: Spray Composition Containing Tranexamic Acid

Composition:

| S. NO | Ingredient | Percent (% w/w) |
|---|---|---|
| 1. | Tranexamic acid | 1.0-3.0% |
| 2. | Chitosan | 0.1-1.0% |
| 3. | PEG 400 | 1.0-5.0% |
| 4. | Polysorbate 80 | 0.1-1.0% |
| 5. | PVP K30 | 0.1-0.5% |
| 6. | Glacial acetic acid | 0.1-2% |
| 7. | Distilled water | Q.s |

Process for Preparation:
1. A required amount of chitosan was dissolved in required quantity of glacial acetic acid
2. To the above solution known amount of Tranexamic acid was added and the solution is kept under continuous stirring.
3. To the above solution required quantities of PEG 400, polysorbate 80 and PVPK 30 is added slowly with continuous stirring and adjusted the volume.
4. The above solution is sterilized by filtration Example-2: Spray Composition Containing Tranexamic Acid Composition:

| S. NO | Ingredient | Percent (% w/w) |
|---|---|---|
| 1. | Tranexamic acid | 2.5% |
| 2. | Chitosan | 0.1-1.0% |
| 3. | PEG400 | 1.0-5.0% |
| 4. | Polysorbate 80 | 0.1-1.0% |
| 5. | PVP K30 | 0.1-0.5% |
| 6. | Glacial acetic acid | 0.1-2% |
| 7. | Distilled water | Q.s |

The process for preparation is similar to that of example-1.

Example-3: Spray Composition Containing Tranexamic Acid

Composition:

| S. NO | Ingredient | Percent (% w/w) |
|---|---|---|
| 1. | Tranexamic acid | 5% |
| 2. | Chitosan | 0.1-1.0% |
| 3. | PEG 400 | 1.0-5.0% |
| 4. | Polysorbate 80 | 0.1-1.0% |
| 5. | PVP K30 | 0.1-0.5% |
| 6. | Glacial acetic acid | 0.1-2% |
| 7. | Distilled water | Q.s |

The process for preparation is similar to that of example-1.

Example-4: Spray Composition Containing Tranexamic Acid

Composition:

| S. NO | Ingredient | Percent (% w/w) |
|---|---|---|
| 1. | Tranexamic acid | 10% |
| 2. | Chitosan | 0.1-1.0% |
| 3. | PEG 400 | 1.0-5.0% |
| 4. | Polysorbate 80 | 0.1-1.0% |
| 5. | PVP K30 | 0.1-0.5% |
| 6. | Glacial acetic acid | 0.1-2% |
| 7. | Distilled water | Q.s |

The process for preparation is similar to that of example-1.

Example 5: Spray Composition Containing Tranexamic Acid

Composition:

| S. NO | Ingredient | Percent (% w/w) |
|---|---|---|
| 1. | Tranexamic acid | 10% |
| 2. | Chitosan | 1.0% |
| 3. | PEG 400 | 5.0% |
| 4. | Polysorbate 80 | 0.2% |
| 5. | PVP K30 | 0.25% |
| 6. | Glacial acetic acid | 1% |
| 7. | Distilled water | Q.s |

The process for preparation is similar to that of example-1.

Example 6: Sterilization by Filtration

The topical spray composition as disclosed in example-5 was sterilized by moist heat sterilization at 121° C. for 10 minutes and 20 minutes respectively and found that there was change in colour of solution due to depolymerisation of chitosan.

Then the composition as disclosed in example-5 was sterilized by filtration method using a pre-filter of 8 μm followed by 0.45 μm and 0.22 μm at a constant pressure of 1.5 bar with a filter surface area of 13 cm$^2$ for one-liter topical spray composition and no decolouration of composition was observed. The time vs filtration rate was depicted in FIG. 1 and filtration time for one-liter spray composition was found to be 12.2 minutes.

Example 7: Biocompatibility Studies

The fibroblasts (L929) cell line obtained from National Centre for Cell Science (NCCS), Pune, India. The cells were grown in growth medium (MEM) supplemented with 10% of Fetal Bovine Serum (FBS, Sigma Aldrich, India) and 100 units/ml of Penicillin/Streptomycin (Sigma Aldrich, India) at 37° C. with humidified air containing 5% of $CO_2$.

Cytotoxic effect of tranexamic acid spray composition as disclosed in example-5 was determined against L929 cell line were tested by MTT assay. Tranexamic acid spray sample showed significant cell proliferation at 3-fold increase when compared to control at 4 hours (FIG. 2) and at 24 hours (FIG. 3). Further the cell proliferation of tranexamic acid spray as disclosed in example-5 was compared with Tranexamic acid spray 75% (75 ml of tranexamic acid spray as disclosed in example-5)+25 ml of complete media containing 10% Fetal bovine serum and Tranexamic acid spray 75% (75 ml of tranexamic acid spray as disclosed in example-5)+25 ml of incomplete media and was depicted in FIG. 2 for 4 hours and FIG. 3 for 24 hours.

The invention claimed is:
1. A topical spray composition consisting of
   (a) about 1% w/w to about 10% w/w tranexamic acid,
   (b) about 0.1% w/w to about 1% w/w chitosan,
   (c) about 1% w/w to about 5% w/w polyethylene glycol,
   (d) about 0.1% w/w to about 1% w/w polysorbate 80,
   (e) about 0.1% w/w to about 0.5% w/w polyvinyl pyrrolidone,
   (f) glacial acetic acid and
   (g) water, wherein the composition is an aqueous solution.
2. The topical spray composition according to claim 1, wherein the composition is used for treating a wound or reducing bleeding at haemorrhaging site.
3. The topical spray composition according to claim 1, wherein the composition is used for the topical treatment of a wound, and the wound is selected from the group consisting of a) minor abrasions, cuts, scrapes, scratches, burns, sunburns, ulcers, internal venous bleeding, external venous bleeding, and b) surgical interventions selected from gastrointestinal surgery, surgery on parenchymal organs; surgical interventions in the ear, nose and throat area (ENT), cardiovascular surgery, aesthetic surgery, spinal surgery, neurological surgery; lymphatic, biliary, and cerebrospinal (CSF) fistulae, air leakages during thoracic and pulmonary surgery, thoracic surgery, orthopaedic surgery; gynaecological surgical procedures; vascular surgery and emergency surgery, liver resection, and soft tissue injury or surgery.

4. The topical spray composition according to claim 1, wherein the composition is topically applied to a traumatic injury in the battle field, a wound or during or after surgery.

5. A topical spray composition consisting of
   (a) about 1% w/w to about 10% w/w tranexamic acid,
   (b) about 0.1% w/w to about 1% w/w chitosan,
   (c) about 1% w/w to about 5% w/w polyethylene glycol,
   (d) about 0.1% to about 1% polysorbate 80,
   (e) about 0.1% to about 0.5% polyvinyl pyrrolidone,
   (f) glacial acetic acid and
   (g) water prepared by a process comprising the steps of
      (i) dissolving Chitosan in 1% glacial acetic acid,
      (ii) dissolving tranexamic acid in above solution,
      (iii) adding polyethylene glycol, polysorbate 80, polyvinyl pyrrolidone and water to above solution and
      (iv) sterilization by filtration using a pre-filter of 8 µm followed by a filter of 0.45 µm and 0.22 µm at constant pressure of 1.5 bar with a filter surface are of 13 cm² for one liter.

* * * * *